United States Patent [19]

Harrison et al.

[11] Patent Number: 5,013,764

[45] Date of Patent: May 7, 1991

[54] CATALYST AND METHOD FOR PRODUCING LOWER ALIPHATIC ALCOHOLS

[75] Inventors: Jeffrey B. Harrison, Fishkill; Chau-Hwa Yang, Hopewell Junction, both of N.Y.

[73] Assignee: Texaco Inc., White Plains, N.Y.

[21] Appl. No.: 389,464

[22] Filed: Aug. 3, 1989

[51] Int. Cl.$^5$ .............................................. C07C 27/06
[52] U.S. Cl. ..................................................... 518/714
[58] Field of Search ......................................... 518/714

[56] References Cited

U.S. PATENT DOCUMENTS 4,298,354 11/1981 Hardman et al. .................... 518/713

Primary Examiner—Howard T. Mars
Attorney, Agent, or Firm—Robert A. Kulason; James J. O'Loughlin; Dominick G. Vicari

[57] ABSTRACT

A catalyst and method are provided for preparing a mixture of lower aliphatic alcohols by reacting a mixture of carbon monoxide and hydrogen under suitable conditions of temperature and pressure in the presence of a catalyst composition comprising palladium, an alkali metal or a mixture of alkali metals and a molybdenum promoter.

23 Claims, No Drawings

CATALYST AND METHOD FOR PRODUCING LOWER ALIPHATIC ALCOHOLS

BACKGROUND OF THE INVENTION

1. Field of the Invention

This invention relates to a method for preparing lower aliphatic alcohols and to the catalyst composition used in said method. More particularly, this invention relates to the production of a mixture of lower aliphatic alcohols in the presence of a novel catalyst composition. The lower aliphatic alcohols so produced are characterized by containing a substantial proportion of alcohols having from 2 to 7 carbon atoms.

2. Description of Background Art

Lower aliphatic alcohols have been proposed as fuel extenders or as replacements for gasoline for fueling internal combustion engines. Certain mixtures of lower aliphatic alcohols have the EPA approval for use and are currently being marketed in the United States. The lower aliphatic alcohols can be produced from domestically available non-petroleum sources. Therefore, their use in fuels would serve to lessen the dependence of the nation on imported petroleum and petroleum products.

Hydrogen and carbon monoxide, or a synthesis gas mixture of hydrogen and carbon monoxide, can be reacted to form lower aliphatic alcohols or hydrocarbons. The synthesis gas feed stream can be produced from non-petroleum sources, such as coal, biomass or other hydrocarbonaceous materials. The synthesis gas mixture itself is produced, for instance, in a partial oxidation reaction of the hydrocarbonaceous material in commercially available processes, such as coal gasification.

Numerous catalysts and catalytic methods have been studied in attempts to provide a viable method for the production of aliphatic alcohols from synthesis gas or from other mixtures of hydrogen and carbon monoxide. Heretofore, the emphasis has been primarily directed to the production of methanol, in the presence of a catalyst composition which is selective for methanol production.

In contrast, the present invention is directed to a method for producing an alcohol mixture containing a substantial amount of aliphatic alcohols having from 2 to 7 carbon atoms. Under selected reaction conditions, this method, when performed in the presence of the novel catalyst composition described hereinbelow, is effective for producing a fraction of higher aliphatic alcohols, i.e., an alcohol fraction consisting of $C_2$ to $C_7$ alcohols, which represents the major or predominant alcohol production in this method.

U.S. Pat No. 1,201,850 discloses a method for the production of hydrocarbons and oxygenated compounds of hydrocarbons by passing an oxide of carbon and hydrogen over a heated catalytic agent under a pressure exceeding 5 atmospheres. A number of catalytic materials are disclosed as well as the fact that a basic compound, such as an alkaline metal hydroxide, can be used with the prescribed catalytic agents.

U.S. Pat. No. 1,625,929 discloses a process for producing methanol in which the catalyst contains copper, cobalt and a metallic halide.

U.S. Pat. No. 3,345,427 discloses a dehydrogenation catalyst and process in which the catalyst consists of nickel, molybdenum and alkali metal oxides on an alumina support.

U.S. Pat. No. 4,096,164 discloses a process for reacting hydrogen and carbon monoxide in the presence of a solid catalyst comprising rhodium with molybdenum or tungsten to produce two carbon atom oxygenated hydrocarbons in which ethanol is the major component.

U.S. Pat. No. 4,199,522 discloses a Fischer-Tropsch process for producing olefins and this disclosure is incorporated herein by reference.

U.S. Pat. Nos. 4,235,801 and 4,246,186 disclose the production of alcohols from a mixture of carbon monoxide and hydrogen in the presence of a rhenium catalyst.

U.S. Pat. No. 4,380,589 discloses a Fischer-Tropsch process for producing hydrocarbons with improved selectivity to $C_2$-$C_4$ olefins by contacting hydrogen and carbon monoxide in the presence of a catalyst. The catalyst disclosed comprises molybdenum, a promoter comprising alkali or alkaline earth metal, and a binder comprising an iron-containing calcium aluminate cement.

U.S. Pat. No. 4,607,055 discloses a process for producing lower aliphatic alcohols from a mixture of carbon monoxide and hydrogen in the presence of a catalyst comprising molybdenum; a metal from the group consisting of cobalt, iron and nickel; and silver. The catalyst is modified by the addition of a promoter from the class consisting of potassium, cesium and rubidium. This disclosure is incorporated herein by reference.

U.S. Pat. No. 4,661,525 discloses a process for producing lower aliphatic alcohols from a mixture of carbon monoxide and hydrogen in the presence of a catalyst comprising molybdenum and a metal selected from the group consisting of cobalt, iron and nickel which has been promoted by an alkali metal selected from the group consisting of potassium, cesium and rubidium. This disclosure is incorporated herein by reference.

Co-assigned application Ser. No. 939,392 filed on Dec. 12, 1986 is directed to a process for producing lower aliphatic alcohols from a mixture of carbon monoxide and hydrogen in the presence of a catalyst comprising rhodium, molybdenum and an alkali metal. This disclosure is incorporated herein by reference.

As previously noted, prior catalytic methods have been notably effective for converting carbon monoxide and hydrogen feedstocks into hydrocarbons or methanol, but none have been particularly effective for providing high yields of a lower aliphatic alcohol mixture characterized by having a substantial amount of alcohols having from 2 to 7 carbon atoms along with the coproduced methanol and/or hydrocarbons.

SUMMARY OF THE INVENTION

It has now been discovered that a mixture of carbon monoxide and hydrogen can be reacted to form a mixture of lower aliphatic alcohols containing a substantial amount of aliphatic alcohols having from 2 to 7 carbon atoms. This reaction is conducted by contacting a carbon monoxide and hydrogen-containing feed mixture, such as synthesis gas, with a novel catalyst composition which exhibits good selectivity for the production of $C_2$-$C_7$ aliphatic alcohols under suitable conditions of temperature and pressure. The catalyst composition comprises an alkali metal, or a mixture of alkali metals, and palladium. Preferably, the alkali metal employed is selected from cesium, potassium, sodium and rubidium or a mixture of same. Most preferably, the alkali metal employed is cesium. The aforedescribed catalyst composition is modified, in accordance with the present invention, by the addition of an amount of a molybdenum promoter to provide the catalyst composition of the present invention, which exhibits good selectivity for the production of $C_2$-$C_7$ aliphatic alcohols.

DETAILED EMBODIMENTS OF THE INVENTION

In accordance with this invention, a mixture of carbon monoxide and hydrogen as, for example, a synthesis gas mixture of said reactants, is reacted over a catalyst comprising an alkali metal or a mixture of alkali metals, and palladium, which has been modified by the addition of a molybdenum promoter. Preferably, the alkali metal employed is selected from cesium, potassium, sodium and rubidium or a mixture of same. Most preferably, the alkali metal employed is cesium. The molybdenum is employed in the catalyst composition at a concentration ranging from about 0.1 to about 6.0 micromoles/$m^2$. A preferred concentration for the molybdenum promoter is from about 0.20 micromoles/$m^2$ to about 1.5 micromoles/$m^2$.

The catalyst can be prepared in a number of ways known in the art. In general, the use of a catalyst support or carrier comprising a relatively refractory, porous, adsorptive and high surface area material is preferred. Conventional carriers or supports, such as alumina, silica, titania, magnesia, silica-alumina, lanthana, zirconia and boron phosphates, are suitable support materials for preparing the catalyst of this invention. Other conventional carriers or supports are to be considered within the scope f this invention. The disclosure in U.S. Pat. No. 4,098,683 is illustrative and is incorporated herein by reference. A particularly preferred support for the present catalyst composition is alumina oxide.

A preferred method for preparing the catalyst is to impregnate a carrier, such as alumina, with a source of palladium, generally in the form of a soluble salt. The impregnated carrier is dried and then calcined according to known procedures. The carrier is thereafter impregnated with a molybdenum salt and is again dried and calcined. Finally, the carrier is impregnated with a salt of an alkali metal or mixture of alkali metals and is again dried and calcined.

In an alternative, but still preferred method for preparing the present catalyst, the sequence can include (a) impregnation of molybdenum onto the support followed by drying and calcining; (b) impregnation of palladium followed by drying and calcining; and (c) impregnation of the alkali metal or mixture of alkali metals followed by drying and calcining. The sequence can also include impregnation followed by drying and calcining of the aforestated components in the following order (a) palladium; (b) alkali metal or mixture of alkali metals; and (c) molybdenum. Again, each of the components are impregnated onto the support in the form of a soluble salt.

The treated or modified catalyst is then subjected to reduction with hydrogen gas generally by heating the promoted catalyst at a temperature of between about 300° C. and 500° C. for an extended period, usually for about 2 to about 8 hours. Preferably, reduction occurs by slowly heating the promoted catalyst to a temperature of about 400° C. in flowing hydrogen gas and at a pressure of about 50 psig for about 4 hours.

The catalyst composition comprises from about 0.5 to about 6.0 weight percent of palladium and from about 2.0 to about 15.0 weight percent of the alkali metal or mixture of alkali metals. The molybdenum promoter is employed in the catalyst composition at about 1.0 to about 10.0 weight percent. The support generally comprises from about 69 to about 97 weight percent of the overall catalyst composition. A preferred composition comprises from about 2.0 to about 5.0 weight percent of palladium, from about 8.0 to about 11.0 weight percent of the alkali metal or mixture of alkali metals and from about 1.0 to about 4.0 weight percent of molybdenum. Again, in a most preferred embodiment, cesium is the alkali metal employed. The amount of molybdenum employed in the catalyst composition is believed to be critical since, if molybdenum is not present in a sufficient quantity, more methanol and less $C_2$-$C_7$ alcohols will be produced, whereas, if too much molybdenum is present, the amount of undesired hydrocarbon side products produced will increase.

The catalyst should have a surface area of about 125 $m^2$/g (square meters per gram of catalyst) or more. A more effective catalyst will have a surface area from about 150 $m^2$/g to about 350 $m^2$/g and the most preferred will have a surface area from about 160 $m^2$/g to about 300 $m^2$/g.

The carbon monoxide and hydrogen employed to form the lower aliphatic alcohols in this process can be provided from any available source. One particularly useful source is synthesis gas produced in the gasification of hydrocarbonaceous materials, such as coals and biomass. An effective gasification process is described in U.S. Pat. No. 3,544,291 wherein a hydrocarbonaceous fuel is partially oxidized with a free oxygen-containing gas in a gas generator. In general, the mole ratio of hydrogen to carbon monoxide employed in this process should range from about 0.1 to about 50 moles of hydrogen per mole of carbon monoxide with the preferred ratio being from about 0.5 to about 5 moles of hydrogen per mole of carbon monoxide.

The reaction conditions for effecting the conversion of the carbon monoxide-hydrogen feed into lower aliphatic alcohols employing the prescribed catalyst of the invention include a reaction temperature ranging from about 240° C. to about 400° C., with a more preferred temperature range being from about 260° C. to about 350° C. The effective pressure range for this process is from about 500 psig to about 3500 psig. The preferred pressure range is from about 750 psig to about 2000 psig.

The space velocity employed to effect the conversion of carbon monoxide and hydrogen over the prescribed catalyst to the aliphatic alcohols is a significant feature of this method. In general, the space velocity, that is the volume of gas passed through a given volume of catalyst per hour expressed as GHSV($hr^{-1}$), must be at least about 1000. A preferred range is from about 5000 to about 50,000. A highly effective process is realized when the space velocity employed ranges from about 10,000 to about 30,000.

The present invention is more fully described in the following Examples which are provided to further illustrate the present invention and should not be construed as limiting the present invention in any way.

In Examples I-IV, the reaction was carried out and tested in a CDS fixed-bed microreactor at a pressure of 1400 psig and a Gas Hourly Space Velocity (GHSV) of 12,000 $hr.^{-1}$. Catalyst activation occurred in the reactor at the temperatures specified in Table I. The hydrogen-carbon monoxide ratio in the synthesis gas feed was 2:1, respectively.

EXAMPLE I

A catalyst was prepared by sequentially impregnating 20 grams of a commercially available alumina oxide carrier (Norton SA-6375B) first with 20 grams of palladium chloride solution to the point of incipient wetness. The resulting precursor (Pd/Al$_2$O$_3$) was dried at room temperature for 24 hours and then calcined in air at 400° C. for 2 hours. 5 grams of the dried and calcined precursor (Pd/Al$_2$O$_3$) was then impregnated with 5 grams of cesium carbonate solution to the point of incipient wetness. The resulting product was dried at 120° C. for 8 hours. The palladium chloride solution was prepared by dissolving 1.504 grams of palladium chloride in 20 ml. of deionized water adjusted to a pH of 1 using hydrochloric acid. The cesium carbonate solution was prepared by dissolving 2.632 grams of cesium carbonate in 20 ml. of deionized water.

EXAMPLE II

A catalyst was prepared by impregnating 5 grams of the dried and calcined precursor from Example I (Pd/Al$_2$O$_3$) with 5 grams of an ammonium heptamolybdate solution to the point of incipient wetness. The resulting product was dried at room temperature for 10 hours and calcined at 400° C. for 2 hours. The product was then impregnated with 5 grams of the cesium carbonate solution used in Example I to the point of incipient wetness and dried at 120° C. for 8 hours. The ammonium heptamolybdate solution was prepared by dissolving 0.188 grams of (NH$_4$)$_6$MO$_7$O$_{24}$.4H$_2$O in 5 ml. of deionized water.

EXAMPLE III

A catalyst was prepared in accordance with Example II except that a more concentrated solution of ammonium heptamolybdate was employed. Specifically, the ammonium heptamolybdate solution used in this Example was prepared by dissolving 0.378 grams of (NH$_4$)$_6$MO$_7$O$_{24}$.4H$_2$O in 5 ml. of deionized water.

EXAMPLE IV

A catalyst was prepared in accordance with Examples II and III except that an even more concentrated solution of the ammonium heptamolybdate was employed. Specifically, the ammonium heptamolybdate solution used in this Example was prepared by dissolving 0.752 grams of (NH$_4$)$_6$MO$_7$O$_{24}$.4H$_2$O in 5 ml. of deionized water.

The catalysts of Examples I–IV were tested for productivity and selectivity towards (C$_2$ to C$_7$) alcohols under the aforestated testing parameters. The results of these tests are provided below in Table I.

TABLE I

|  | Unmodified Catalyst of Example I | Modified Catalyst of | | |
| --- | --- | --- | --- | --- |
|  |  | EX. II | EX. III | EX. IV |
| Composition (wt %) | | | | |
| Pd | 3.9 | 3.8 | 3.7 | 3.7 |
| Mo | — | 1.7 | 3.3 | 6.4 |
| Cs | 9.6 | 9.0 | 8.7 | 8.5 |
| Alumina | 86.5 | 85.5 | 84.3 | 81.4 |
| Reactor Temp (°C.) | 300 | 294 | 297 | 297 |
| Alc. Prod. (g/g-hr) | 0.17 | 0.20 | 0.23 | 0.15 |
| Alc. Sel. (%, CO$_2$ free) | 87.8 | 72.5 | 71.0 | 66.6 |
| Alc. Comp., (wt %) (methanol) | 98.3 | 82.2 | 82.5 | 82.6 |
| (C$_2$-C$_7$ alcohols) | 1.7 | 17.8 | 17.5 | 17.4 |
| Mole Ratio (C$_s$/Pd/Mo) | 2/1/0 | 1.9/1/.5 | 1.9/1/1 | 1.9/1/2 |

As these data demonstrate, the unpromoted catalyst of Example I produces mainly methanol at 0.17 g/g-hr at 300° C. The molybdenum promoted catalyst of Examples II–IV, on the other hand, produce a mixture of methanol and C$_2$–C$_7$ higher alcohols at a higher production rate.

The catalysts of Examples II and III were further tested under the aforestated conditions; however, the hydrogen-carbon monoxide ratio in the synthesis gas feed was 1:1. The results of the tests and the reaction temperatures employed are provided below in Table II.

TABLE II

|  | Modified Catalyst of | |
| --- | --- | --- |
|  | Example II | Example III |
| Reactor Temperature (°C.) | 292 | 305 |
| Alc. Prod. (g/g-hr) | 0.14 | 0.21 |
| Alc. Sel. (%, CO$_2$ free) | 78.0 | 68.6 |
| Alc. Comp. (wt. %) | | |
| (methanol) | 79.4 | 74.9 |
| (C$_2$-C$_7$) alcohol | 20.6 | 25.1 |

The catalyst of Example III was further tested under the aforestated conditions; however, the hydrogen-carbon monoxide ratio in the synthesis gas feed was 4:1, respectively. The results of the test and the reaction temperature employed are provided below in Table III.

TABLE III

|  | Modified Catalyst of Example III |
| --- | --- |
| Reaction Temperature (°C.) | 296 |
| Alc. Prod. (g/g-hr.) | 0.22 |
| Alc. Sel. (%, CO$_2$ free) | 71.0 |
| Alc. Comp. (wt. %) | |
| (methanol) | 82.8 |
| (C$_2$-C$_7$ alcohols) | 17.2 |

What is claimed is:

1. A method for preparing lower aliphatic alcohols which comprises reacting carbon monoxide and hydrogen in the presence of a catalyst composition which includes palladium, an alkali metal or a mixture of alkali metals and which has been modified by a molybdenum promoter, said catalyst composition being devoid of copper and thorium.

2. The method of claim 1 wherein said alkali metal or mixture of alkali metals is selected from the group consisting of cesium, potassium, sodium or rubidium.

3. The method of claim 1 wherein said alkali metal is cesium.

4. The method of claim 1 wherein said catalyst composition further includes a support for supporting said palladium, said alkali metal or mixture of alkali metals and said molybdenum promoter.

5. The method of claim 4 wherein said support is selected from the group consisting of alumina, silica, titania, magnesia, silica-alumina, lanthana, zirconia or boron phosphates.

6. The method of claim 5 wherein said support is alumina oxide.

7. The method of claim 1 wherein said reaction takes place at a temperature of about 240° C. to about 400° C.

8. The method of claim 7 wherein said reaction takes place at a temperature of about 260° C. to about 350° C.

9. The method of claim 1 wherein said reaction takes place at a pressure of about 500 psig to about 3500 psig.

10. The method of claim 9 wherein said reaction takes place at a pressure of about 750 psig to about 2000 psig.

11. The method of claim 1 wherein said reaction takes place at a gas hourly space velocity of at least about 1000 $hr^{-1}$.

12. The method of claim 11 wherein said reaction takes place at a gas hourly space velocity of between about 10,000 $hr^{-1}$ to about 30,000 $hr^{-1}$.

13. The method of claim 1 wherein said molybdenum promoter is employed at a concentration of about 0.1 micromoles/$m^2$ to about 6.0 micromoles/$m^2$.

14. The method of claim 1 wherein said catalyst composition includes from about 0.5 to about 6.0 weight percent of palladium; from about 2.0 to about 15.0 weight percent of said alkali metal or mixture of alkali metals and from about 1.0 to about 10 weight percent of molybdenum.

15. The method of claim 14 wherein said catalyst composition includes from about 2.0 to about 5.0 weight percent palladium; from about 8.0 to about 11.0 weight percent of said alkali metal or mixture of alkali metals and from about 1.0 to about 4.0 weight percent of molybdenum.

16. The method of claim 4 wherein said support comprises from about 69 to about 97 weight percent of said catalyst composition.

17. The method of claim 1 wherein the molar ratio of said hydrogen to said carbon monoxide is in the range of from about 0.1:1 to about 50:1.

18. The method of claim 1 wherein the source of said carbon monoxide and hydrogen is synthesis gas.

19. The method of claim 1 wherein said catalyst composition has a surface area ranging from about 150 $m^2/g$ to about 350 $m^2/g$.

20. A method for preparing lower aliphatic alcohols which comprises reacting carbon monoxide and hydrogen in the presence of a catalyst composition at a temperature of about 240° C. to about 400° C., at a pressure of about 500 psig to about 3500 psig and at a gas hourly space velocity of at least about 1000 $hr^{-1}$, said catalyst composition including from about 0.5 to about 6.0 weight percent of palladium, from about 2.0 to about 15.0 weight percent of an alkali metal or a mixture of alkali metals and from about 1.0 to about 10 weight percent of a molybdenum promoter, said molybdenum promoter being employed at a concentration ranging from about 0.1 micromoles/$m^2$ to about 6.0 micromoles/$m^2$ and said catalyst composition being devoid of copper and thorium.

21. The method of claim 20 wherein said alkali metal or mixture of alkali metals is selected from the group consisting of cesium, potassium, sodium or rubidium.

22. The method of claim 20 wherein said alkali metal is cesium.

23. The method of claim 20 wherein said catalyst composition includes from about 2.0 to about 5.0 weight percent of palladium, from about 8.0 to about 11.0 weight percent of said alkali metal or mixture of alkali metals and from about 1.0 to about 4.0 weight percent of said molybdenum promoter.

* * * * *